United States Patent
Hilfiker et al.

(10) Patent No.: US 8,765,742 B2
(45) Date of Patent: Jul. 1, 2014

(54) CRYSTALLINE METHYLTHIONINIUM CHLORIDE HYDRATES

(75) Inventors: Rolf Hilfiker, Basel (CH); Timo Rager, Basel (CH)

(73) Assignee: Wista Laboratories Ltd., Singapore (SG)

( * ) Notice: Subject to any disclaimer, the term of this patent is extended or adjusted under 35 U.S.C. 154(b) by 183 days.

(21) Appl. No.: 13/497,686

(22) PCT Filed: Sep. 23, 2010

(86) PCT No.: PCT/IB2010/002526
§ 371 (c)(1), (2), (4) Date: Mar. 22, 2012

(87) PCT Pub. No.: WO2011/036558
PCT Pub. Date: Mar. 31, 2011

(65) Prior Publication Data
US 2012/0238556 A1    Sep. 20, 2012

Related U.S. Application Data

(60) Provisional application No. 61/245,391, filed on Sep. 24, 2009.

(51) Int. Cl.
C07D 279/18     (2006.01)
A61K 31/5415    (2006.01)

(52) U.S. Cl.
USPC ...................................... 514/225.2

(58) Field of Classification Search
USPC .......................... 544/35; 514/225.2
See application file for complete search history.

(56) References Cited

FOREIGN PATENT DOCUMENTS

WO    WO 2007/110629 A1    10/2007
WO    WO 2008/124220 A1    10/2008

OTHER PUBLICATIONS

Rager, et al., "The crystalline state of methylene blue: a zoo of hydrates", *Physical Chemistry Chemical Physics*, 2012, doi.org/10.1039/c2cp40128B.
The International Search Report received in the corresponding International Application No. PCT/IB2010/002526, dated Sep. 5, 2011.
Budavari (Editor): "6137 Methylene Blue", Merck Index. Encyclopedia of Chemicals, Drugs, and Biologicals, Jan. 1996, p. 6142. (XP002628304).
Bodman, et al., "Solubility and Properties of Two Crystalline Phases of Methylene Blue", Journal of Chemical and Engineering Data, vol. 12, No. 4, 1967, pp. 500-504.
Caira., "Crystalline Polymorphism of Organic Compounds", Topics in Current Chemistry, vol. 198, 1998, pp. 163-208. (XP001156954).
Dahne S., "Die rote Form des Methylenblaus", Zietschrift Fuer Physikalische Chemie, Geest & Portig, vol. 220, 1962, pp. 187-198. (XP009143176).
Kobayashi, et al., "Spontaneous formation of an ordered structure during dip-coating of methylene blue on fused quartz", Chemical Physics Letters, vol. 349, 2001, pp. 376-382. (XP002616890).
Marr III, et al., "The crystal structure of methylene blue pentahydrate", Acta Crystallographica, Section B, vol. b29, No. 4, 1973, pp. 847-853.
Tardivo, et al., "Methylene blue photodynamic therapy: From basic mechanisms to clinical applications", Photodiagnosis and Photodynamic Therapy, vol. 2, No. 3, 2005, pp. 175-191. (XP005194872).
Warwicker, "The Crystal Structure of Methylene-blue", Journal of the Chemical Society, Jan. 1955, p. 2531. (XP009143230).
Zhdanov G.S. et al., "X-ray structural study of a methylene blue dye", Soviet Physics Crystallography, vol. 1, No. 1, 1956, pp. 44-47. (XP009143188).

*Primary Examiner* — Kahsay Habte
(74) *Attorney, Agent, or Firm* — Foley & Lardner LLP

(57) ABSTRACT

Three dihydrate forms B, C and D and a monohydrate form E of methylthioninium chloride are described. Forms B, C, D and E can be prepared under controlled humidity and temperature from methylthioninium chloride with higher water content or conversion of a hydrate. The hydrates can be incorporated in pharmaceutical compositions.

14 Claims, 2 Drawing Sheets

CRYSTALLINE METHYLTHIONINIUM CHLORIDE HYDRATES

CROSS-REFERENCE TO RELATED PATENT APPLICATIONS

This application is the U.S. National Phase of PCT/IB2010/002526, filed Sep. 23, 2010, and which claims priority from U.S. Provisional Application No. 61/245,391, filed Sep. 24, 2009, all of which are incorporated herein by reference in entirety.

The present invention relates to crystalline methylthioninium chloride hydrates, in particular methylthioninium chloride dihydrate form B, methylthioninium chloride dihydrate form C, methylthioninium chloride dihydrate form D and methylthioninium chloride monohydrate form E; the processes for the preparation of forms B, C, D and E; and to, preferably pharmaceutical, compositions comprising forms B, C, D and E.

Methylthioninium chloride (MTC) [Methylene Blue: 3,7-bisdimethylaminophenazothionium chloride, $C_{16}H_{16}ClN_3S$, 319.85 g/mol] was prepared for the first time in 1876 (*The Merck Index*, 13th edition, Merck & Co., Inc., 2001, entry 6085). Various synthesis methods are known and have recently been summarized in WO 2006/032879. WO 2006/032879 also states a number of applications of methylene blue, which include the use as a medical dye, as a redox indicator, an antiseptic, for the treatment and prevention of kidney stones, the treatment of melanoma, malaria, viral infections, and Alzheimer's disease. MTC has also been used as an oxidizing agent and as an antidote in the case of CO, nitrite and aniline poisoning.

MTC is known to exist in the form of hydrates. For example, the Fluke catalogue states in very general terms that MTC may contain up to 22% water [Fluke Catalogue 1997/1998, Fluka Chemie AG, 1997]. Structures with from one to five molecules of water have been formulated in the literature [J. O. Warwicker, *J. Chem. Soc.* (1955) 2531; G. F. Davidson, *J. Textile Institute* 38 (1947) T408-418]. The formation of a trihydrate has apparently found widespread acceptance [e.g. *The Merck Index*, 13th edition, Merck & Co., Inc., 2001, entry 6085]. However, this claim was already disputed more than 80 years ago, and the non-specific adsorption of water by MTC was proposed instead [H. Wales, O. A. Nelson, *J. Am. Chem. Soc.* 45 (1923) 1657; C. M. Martin, J. W. G. Neuhaus, F. H. Reuter, *Analyst* 71 (1946) 29-31].

To date, the only hydrate that has been characterized in detail is a pentahydrate of MTC [J. O. Warwicker, *J. Chem. Soc.* (1955) 2531; H. E. Marr III, J. M. Stewart, M. F. Chiu, *Acta Cryst.* B29 (1973) 847]. For this hydrate, even single crystal X-ray data are available. It consists of n-stacked columns of methylthioninium cations that are arranged in planes perpendicular to the α-axis of the crystal. The water molecules and chloride ions are located between these layers, whereby the chloride ions are concentrated in planes almost perpendicular to the water planes and parallel to the axis of the columns. The chloride ions are coordinated with three hydrogen bonds from 3/2 water molecules.

Presumably the same structure was earlier attributed to a tetrahydrate [W. H. Taylor, *Z. Krist.* 91 (1935) 450]. A phase transition between the pentahydrate and a second polymorphic form was described to occur near 30° C. in aqueous suspension [S. W. Bodman, S. P. Kodama, P. C. Pfeil, R. E. Stevens, *J. Chem. Eng. Data* 12 (1967) 500]. The second form was also obtained by vacuum drying of the pentahydrate at room temperature, and its water content was indicated to amount to approximately 1 mol/mol.

The solid state form of a compound is of great importance for pharmaceutical applications. It may influence the chemical and physical stability of the compound itself and of its formulations, may have an impact on pharmacokinetics and bioavailability. In the case of hydrates, the composition has also an influence on the correct dosage of the active pharmaceutical ingredient.

Methylthioninium chloride used in pharmaceutical compositions is described as a trihydrate (USP Material Safety Data Sheet for Methylene Blue (Catalogue Number 1428008), 2005), which is thought to be methylthioninium chloride pentahydrate admixed with other components. The mixture or components in the mixture are stable under different conditions, they may convert to other polymorphic or pseudopolymorphic species and hence change their composition, so that correct dosage is a problem and storage stability may be considered to be insufficient.

The present invention provides specific polymorphic forms of methylthioninium chloride hydrates, as well as safe and reproducible processes for their preparation. The present invention also provides specific polymorphic forms of methylthioninium chloride hydrates, which are stable under defined conditions, and which have good solubility and bioavailability. The present invention provides specific polymorphic forms of methylthioninium chloride hydrates, which can be easily metered to arrive at defined contents in pharmaceutical compositions in order to administer exact amounts of the active compound.

A first aspect of the present invention is MTC substantially in crystalline Form B of methylthioninium chloride dihydrate.

In some embodiments, Form B is not exactly a dihydrate, but may contain a small amount of water (for example, ~0.2-0.3 equivalents) in excess of the dihydrate. However, for convenience it is referred to herein as crystalline Form B of methylthioninium chloride dihydrate.

Crystalline Form B of methylthioninium chloride dihydrate has a X-ray powder diffraction pattern (wavelength 1.54180 Å) containing specific peaks at the following 2θ values (±0.1°): 5.8, 11.2, 25.3, 26.8.

Crystalline Form B of methylthioninium chloride dihydrate may also have the following additional peaks in a X-ray powder diffraction pattern at the following 2θ values (±0.1°): 15.6, 16.9, 20.3, 28.3.

Crystalline Form B of methylthioninium chloride dehydrate may also be characterized by any combination of three or more peaks selected from the list of 8 peaks above, with a preference given to peaks at low angles.

A representative powder XRD pattern of crystalline methylthioninium chloride dihydrate Form B is shown in FIG. 1.

Without wishing to be bound by theory, Form B is a thermodynamically metastable form at room temperature over the whole range of relative humidity. Powder X-ray and DSC indicate the crystalline character of form B. Thermogravimetry (TG, heating rate 10° C./min) results in a water loss of 10.6% or of 10.9 to 11.5% between room temperature and 150° C., corresponding to a water content of about 2, for example 2.2-2.3 water molecules per molecule methylene blue. The TG analysis enables Form B to be distinguished from Forms A and E.

Form B may also be characterized using Differential Scanning calorimetry (DSC). When subject to DSC, with a heating rate 100° C./min in a gold crucible, Form B has a melting peak at 186° C. with a shoulder towards lower temperature. When subject to DSC, with a heating rate of 20° C./min in a gold crucible, Form B exhibits a small endothermic peak near 100°

C. and a melting peak at 183° C. with a shoulder towards lower temperature. The melting peak is immediately followed by decomposition.

Form B may also be characterized using attenuated total reflection infrared (ATR-IR) spectroscopy. Characteristic IR signals of form B are found at 1068, 877, and 839 cm$^{-1}$.

The crystalline Form B is obtained as a greenish powder.

Methylthioninium chloride dihydrate Form B is soluble in methanol and acetic acid and possesses a low to moderate solubility in water, hydrochloric acid and other organic solvents. Its solubility is similar to that of methylthioninium chloride pentahydrate Form A.

An other aspect of the present invention is a process for the preparation of Form B, which comprises drying of solid Form A methylthioninium chloride pentahydrate at an elevated temperature and low humidity. The temperature is preferably at least 40° C., or even 50° C., and may be less than 70° C. In preferred embodiments, the temperature is about 60° C. The humidity is preferably below 40% r.h, and is more preferably about 35% r.h., or lower. The drying should continue for sufficient time to achieve conversion to Form B.

A further aspect of the present invention is a process for the preparation of crystalline methylthioninium chloride dihydrate Form B, which comprises exposing solid methylthioninium chloride pentahydrate Form A at ambient temperature to an inert gas flow having a relative humidity from 8 to 15%.

The relative humidity is preferably from 9 to 12% at room temperature. Examples for inert gases are air, nitrogen, helium, neon, argon and krypton, or mixtures thereof. The solid methylthioninium chloride pentahydrate Form A is preferably in the form of a crystalline powder, which may be agitated to accelerate the drying operation. The exposure time depends on the amount of methylthioninium chloride pentahydrate Form A and may range from hours to several weeks.

Ambient temperature may mean a temperature from 15 to 30° C. and preferably 20 to 25° C.

The present inventors have also found that methylthioninium chloride exists in at least two further crystalline dihydrate forms, hereinafter called forms C and D.

A further aspect of the present invention is a crystalline Form C of methylthioninium chloride dihydrate.

Crystalline Form C of methylthioninium chloride dihydrate has a characteristic X-ray powder diffraction pattern containing specific peaks at the following 2θ values (±0.1°): 8.1, 11.1, 17.6, 25.9, 27.2.

Crystalline Form C of methylthioninium chloride dihydrate may also have the following additional peaks in a X-ray powder diffraction pattern at the following 2θ values (±0.1°): 16.2, 17.8, 24.4, 30.8, 31.3, 33.0.

Crystalline Form C of methylthioninium chloride dihydrate may also have the following further peaks in a X-ray powder diffraction pattern at the following 2θ values (±0.1°): 13.4, 18.4, 28.7, 29.5, 30.0, 34.1, 36.0, 36.7, 39.5, 42.7, 45.3, 48.0.

Crystalline Form C of methylthioninium chloride dihydrate may also be characterized by any combination of five or more peaks selected from the list of 23 peaks above, with a preference given to peaks at low angles.

A representative powder XRD pattern of crystalline methylthioninium chloride dihydrate Form C is shown in FIG. 2.

Without wishing to be bound by theory, Form C is the thermodynamically stable form at room temperature and a relative humidity, of less than 40% and down to about 10%, or possibly even down to 4%. This broad range of therrriddynamic stability (compared to Forms B, D or E), which in addition broadens at higher temperatures, makes Form C the form of choice for preparation processes, storage or use above temperatures of 25° C. Powder X-ray diffraction and DSC indicate the crystalline character of form C. Thermogravimetry (TG), with a heating rate of 10° C./min, indicates a water loss of about 9.8 to 11.4% between room temperature and 150° C. corresponding to a water content of about 1.9 to 2.3 water molecules per molecule methylene blue. In preferred embodiments, thermogravimetry with a heating rate 10° C./min indicated a water loss of about 9.8 to 10.7% between room temperature and 150° C., in two steps. The total water loss corresponds to a water content of almost exactly two water molecules per molecule methylene blue. The presence of two steps is characteristic of the TG profile of Form C. The TG analysis enables Form C to be distinguished from Forms A and E.

Form C may also be characterized using Differential Scanning calorimetry (DSC). When subject to DSC, with a heating rate of 100° C./min in a gold crucible, Form C has two endothermic maxima at 151° C. and 183° C.

Form C may also be characterized using attenuated total reflection infrared (ATR-IR) spectroscopy. Characteristic IR signals of form C are found at 1497/1483 (double peak), 1438, 1301, and 1060 cm$^{-1}$.

The crystalline form C is obtained as a greenish powder with a golden luster.

A further aspect of the invention is a process for the preparation of Form C by re-crystallization of water containing methylthioninium chloride or specific hydrates from dimethylsulfoxide.

Form C can also be prepared by suspension equilibration of Forms A or B or other polymorphic forms in acetonitrile or isopropanol in the presence of small amounts of water. Therefore, another aspect of the present invention is a process for the preparation of methylthioninium chloride dehydrate Form C, wherein a water containing methylthioninium chloride or a mixture of various hydrates or a specific hydrate of methylthioninium chloride is suspended and stirred at ambient temperature in a solvent selected from the group comprising isopropanol, 1-propanol, 1-butanol, 2-butanol, tert-butanol, tetrahydrofurane, dioxane, acetone, 2-butanone, and acetonitrile, or mixtures thereof, containing a small amount of water.

The selected organic solvents including mixtures of at least two solvent preferably possess a poor solubility for MTC dihydrate Form C at the temperature of isolation of this crystalline product, which is typically at room temperature or below. A solubility of less than 20 g/l and in particular less than 2 g/l at room temperature is preferred. The solvent is miscible with water, and its vapor pressure preferably exceeds the one of water.

The amount of hydrates in the suspension may be from 1 to 70%, preferably from 5 to 60%, more preferably from 5 to 50% and particularly preferred from 10 to 40% by weight, referred to the amount of solvent. Ambient temperature may mean a temperature from 15 to 30° C. and preferably 20 to 25° C.

The appropriate small amount of water depends on the amount of water already provided by the methylthioninium chloride hydrates added initially, the concentration of methylthioninium chloride in the suspension, and the water activity in the chosen solvent as a function of water content. When conducted at room temperature, the water content at the end of the transformation process has to correspond to a water activity between 0.04 and 0.4, preferably 0.1 and 0.3 (corresponding to 4 to 40 respectively 10 to 30% relative humidity).

The treatment should be long enough for conversion of the other forms into Form C. The treatment time mainly depends on the amount of solid in the suspension and the composition of the starting material and may be from hours to several days.

Following conversion into Form C, the solid may be isolated. Isolating of the solid is carried out by filtration. Following isolation solvent may be removed from Form C. Removal of solvent may be carried out in vacuum and at a temperature below 100° C., preferably below 50° C., and most preferred close to room temperature. Alternatively, a gas flow with a relative humidity, which corresponds to the stability range of the hydrate, may be passed over the sample for drying.

A further aspect object of the present invention is crystalline Form D of methylthioninium chloride dihydrate.

Crystalline Form D of methylthioninium chloride dihydrate has a X-ray powder diffraction pattern containing specific peaks at the following 2θ values (±0.1°): 7.0, 8.5, 12.0, 14.4, 25.3, 25.7, 27.5.

Crystalline Form D of methylthioninium chloride dihydrate may also have the following additional peaks in a X-ray powder diffraction pattern at the following 2θ values (±0.1°): 6.0, 10.4, 20.9, 21.1, 21.7, 22.3, 23.7, 24.5, 26.9, 28.5, 29.0, 30.4, 31.8.

Crystalline Form D of methylthioninium chloride dihydrate may also have the following further peaks in a X-ray powder diffraction pattern at the following 2θ values (±0.1°): 9.8, 16.3, 17.1, 18.1, 34.9, 41.5, 46.5.

Crystalline Form D of methylthioninium chloride dihydrate may also be characterized by any combination of five or more peaks selected from the list of 27 peaks above, with a preference given to peaks at low angles.

A representative powder XRD pattern of crystalline methylthioninium chloride dihydrate Form D is shown in FIG. 3.

Without wishing to be bound by theory, Form D is thermodynamically metastable at room temperature and over the whole range of relative humidity. Powder X-ray diffraction and DSC indicate the crystalline character of form D. Thermogravimetry (TG, heating rate 10° C./min) results in a water loss of about 9.3 to 11.2% between room temperature and 150° C., corresponding to a water content of about 1.9 to 2.3 water molecules per molecule methylene blue. The TG analysis enables Form D to be distinguished from Forms A and E.

Form D may also be characterized using Differential Scanning calorimetry (DSC). When subject to DSC, with a heating rate 100° C./min in a gold crucible, Form D has two endothermic peak maxima at 164° C. and 185° C. and a step in the baseline is observed near 63° C.

Form D may also be characterized using attenuated total reflection infrared (ATR-IR) spectroscopy. Characteristic IR signals of form D are found at 1181, 1140, 1066, 951, and 831 cm$^{-1}$.

The crystalline form D is obtained as a grey to violet powder.

Pure form D can be prepared by precipitation processes such as the addition of a solution in a good solvent to a large excess of a non-solvent. Accordingly, a further aspect of the invention is a process for the preparation of methylthioninium chloride dihydrate Form D, comprising dissolving methylthioninium chloride pentahydrate Form A in methanol and combining the solution with t-butyl-methyl ether, either by adding t-butyl-methyl ether to the methanolic solution or by adding the methanolic solution to t-butyl methyl ether.

A further aspect of the invention is a process for the preparation of essentially pure methylthioninium chloride dihydrate Form D, comprising dissolving methylthioninium chloride pentahydrate Form A in acetic acid and combining the solution with toluene, either by adding toluene to the acetic acid solution or by adding the acetic acid solution to toluene.

The concentration of Form A in the methanol or acetic acid solution may range from 1 to 30% by weight and preferably from 5 to 20% by weight, based on the amount of methanol or acetic acid. The amount of t-butyl-methyl ether or toluene may be equal to the volume of methanol or acetic acid, but preferably exceeds this volume by at least a factor of 5, more preferably by a factor of 10.

After precipitation of Form D in either of the above two methods, the solid may be isolated by filtration. After isolation, the solvent may be removed from Form D. The solvent is removed by vacuum drying or in an inert gas flow, whereby the relative air humidity in all process steps is less than 50%, and preferably less than 40%.

The present inventors have also found that methylene blue forms a crystalline monohydrate.

A further aspect of the present invention is crystalline Form E methylthioninium chloride monohydrate.

Crystalline Form E methylthioninium chloride monohydrate has a characteristic X-ray powder diffraction pattern containing specific peaks at the following 2θ values (±0.1°): 9.0, 12.5, 14.1, 14.4, 18.1, 23.2, 24.1, 26.0.

Crystalline Form E methylthioninium chloride monohydrate may also have the following additional peaks in a X-ray powder diffraction pattern at the following 2θ values (±0.1°): 24.5, 27.2.

Crystalline Form E methylthioninium chloride monohydrate may also have the following further peaks in a X-ray powder diffraction pattern at the following 2θ values (±0.1°): 21.8, 22.1, 28.4, 29.6, 32.0, 39.3, 41.7, 47.1.

Crystalline Form E methylthioninium chloride monohydrate may also be characterized by any combination of five or more peaks selected from the list of 18 peaks above, with a preference given to peaks at low angles.

A representative powder XRD pattern of crystalline methylthioninium chloride monohydrate Form E is shown in FIG. 4.

Without wishing to be bound by theory, Form E is thermodynamically stable at room temperature at a relative humidity of less than about 10%, or less than about 4%, and down to about 2%. Powder X-ray diffraction indicates the crystalline character of form E.

Thermogravimetry (TG, heating rate 10° C./min) results in a water loss of 5.1% to 5.4% between room temperature and 110° C., corresponding to a water content of one water molecule per molecule methylene blue. TG can be used to distinguish Form E from forms A, B, C and D.

Form E may also be characterized using Differential Scanning calorimetry (DSC). When subject to DSC, with a heating rate of 100° C./min in a gold crucible, Form E shows no thermal event up to the decomposition temperature near 220° C.

Form E may also be characterized using attenuated total reflection infrared (ATR-IR) spectroscopy. Characteristic IR signals of form E are found at 1350, 1323, 1242, 1218, 1175, 1134, and 1035 cm$^{-1}$.

The crystalline form E is obtained as an ocher colored powder.

Pure form E can be prepared by suspension equilibration of water containing methylthioninium chloride or forms A, B, C or D or mixtures thereof under dry conditions in a solvent. Suitable solvents include those used in the suspension equilibration for the preparation of methylthioninium chloride dihydrate form C, namely isopropanol, 1-propanol, 1-butanol, 2-butanol, 2-methyl-2-butanol, tetrahydrofurane, dioxane, acetone, 2-butanone, and acetonitrile. Accordingly, another aspect of the present invention is a process for the preparation of crystalline methylthioninium chloride monohydrate form E, wherein water containing methylthioninium chloride or a mixture of various hydrates or a specific hydrate of methylthioninium chloride is suspended and stirred at ambient temperature in a dry solvent, preferably isopropanol.

The amount of hydrates in the suspension may be from 1 to 70%, preferably from 5 to 60%, more preferably from 5 to 50% and particularly preferred from 10 to 40% by weight, referred to the amount of non-solvent. Ambient temperature may mean a temperature from 15 to 35° C. and preferably 20 to 35° C. A temperature cycle from 20 to 35° C. within for example 30 minutes may be applied to facilitate water removal. Dry isopropanol means a water content of less than 1% by weight in isopropanol, preferably less than 0.1% by weight.

The treatment time should be sufficient to allow for conversion to Form E. The treatment time mainly depends on the amount of solid in the suspension and may be from hours to several weeks. After an appropriate equilibration time, the solvent may have to be removed and be replaced by new, dry solvent in order to keep the water content low.

After formation of Form E, the solid may be isolated. Isolating of the solid is carried out by filtration. After isolation of the solid, solvent may be removed from Form E. Removal of solvent may be carried out in vacuo and at a temperature below 100° C., preferably below 50° C., and most preferred close to room temperature. Alternatively, a gas flow with a relative humidity, which corresponds to the stability range of the hydrate, may be passed over the sample for drying.

Purity

In each of the above aspects, methylthioninium chloride is preferably substantially in the Form described. "Substantially in the Form described" means that at least 50% by weight of methylthioninium chloride is in the Form described, preferably at least 70% by weight, 80% or 90% by weight. In some embodiments, at least 95% by weight, 99% by weight or even 99.5% or more by weight may be in the crystalline form described.

In each of the above aspects, methylthioninium chloride is preferably substantially free from solvent. The term "substantially free from solvent" as used herein refers to the form having only insignificant amounts of any solvent, e.g. a form with a total of 0.5% by weight or less of any solvent. The total amount of any solvent may be 0.25%, 0.1%, 0.05% or 0.025% by weight or less.

Compositions

One aspect of the present invention pertains to compositions comprising methylthioninium chloride dihydrate Form B, C or D or methylthioninium chloride monohydrate Form E, as described herein.

In one embodiment, the composition further comprises a pharmaceutically acceptable carrier, diluent, or excipient.

Methods of Inactivating Pathogens

One aspect of the present invention pertains to use of methylthioninium chloride dihydrate Form B, C or D or methylthioninium chloride monohydrate Form E, as described herein, in a method of inactivating a pathogen in a sample (for example a blood or plasma sample), the method comprising introducing the compound into the sample, and exposing the sample to light.

Methods of Medical Treatment

One aspect of the present invention pertains to a methylthioninium chloride dihydrate Form B, C or D or methylthioninium chloride monohydrate Form E, as described herein, for use in a method of treatment (e.g., of a disease condition) of the human or animal body by therapy.

One aspect of the present invention pertains to use of methylthioninium chloride dihydrate Form B, C or D or methylthioninium chloride monohydrate Form E, as described herein, for the manufacture of a medicament for use in the treatment of a disease condition.

One aspect of the present invention pertains to use of methylthioninium chloride dihydrate Form B, C or D or methylthioninium chloride monohydrate Form E, as described herein, in the treatment of a disease condition.

One aspect of the present invention pertains to a method of treatment of a disease condition in a patient, comprising administering to said patient a therapeutically-effective amount of methylthioninium chloride dihydrate Form B, C or D or methylthioninium chloride monohydrate Form E, as described herein.

Disease Conditions

In one embodiment, the disease condition is a tauopathy.

A "tauopathy" is a condition in which tau protein (and aberrant function or processing thereof) plays a role. Alzheimer's Disease is an example of a tauopathy. The pathogenesis of neurodegenerative disorders such as Pick's disease and Progressive Supranuclear Palsy (PSP) appears to correlate with an accumulation of pathological truncated tau aggregates in the dentate gyms and stellate pyrapidal cells of the neocortex, respectively. Other dementias include fronto-temporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see, e.g., Wischik, C. M., Theuring, F. & Harrington, C. R. (2000) The molecular basis of tau protein pathology in Alzheimer's disease and related neurodegenerative dementias. In Neurobiology of Alzheimer's Disease (Eds. D. Dawbarn & S. J. Allen) Oxford University Press, Oxford, 103-206, especially Table 5.1 therein). Each of these diseases, which is characterized primarily or partially by abnormal tau aggregation, is referred to herein as a "tauopathy."

In one embodiment, the disease condition is Alzheimer's disease (AD).

In one embodiment, the disease condition is skin cancer.

In one embodiment, the disease condition is melanoma.

In one embodiment, the disease condition is viral, bacterial or protozoal.

In one embodiment, the protozoal disease condition is malaria. In this embodiment treatment may be in combination with another antimicrobial agent e.g. in combination with chloroquine or atovaquone.

In one embodiment, the viral disease condition is caused by Hepatitis C, HIV or West Nile virus.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously.

Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Routes of Administration

Methylthioninium chloride dihydrate Form B, C or D or methylthioninium chloride monohydrate form E, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal—(e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrastemal (including, e.g., intracatheter injection into the brain); by implant of a depot or reservoir, for example, subcutaneously or intramuscularly.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for methylthioninium chloride dihydrate Form B, C or D or methylthioninium chloride monohydrate form E to be used (e.g., administered) alone, it is often preferable to present it as a composition or formulation.

In one embodiment, the composition is a pharmaceutical composition (e.g., formulation, preparation, medicament) comprising methylthioninium chloride dihydrate form B, C or D or methylthioninium chloride monohydrate form E, as described herein, and a pharmaceutically acceptable carrier, diluent, or excipient.

In one embodiment, the composition is a pharmaceutical composition comprising at least methyithioninium chloride dihydrate Form B, C or D or methyithioninium chloride monohydrate Form E, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, N.Y., USA), Remington's Pharmaceutical Sciences, 20th edition, pub. Lippincott, Williams & Wilkins, 2000; and Handbook of Pharmaceutical Excipients, 2nd edition, 1994.

Another aspect of the present invention pertains to methods of making a pharmaceutical composition comprising admixing [$^{11}$C]-radiolebelled methyithioninium chloride dihydrate Form B, C or D or methyithioninium chloride monohydrate Form E, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringers Solution, or Lactated Ringers Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Examples of Preferred Formulations

One aspect of the present invention pertains to a dosage unit (e.g., a pharmaceutical tablet or capsule) comprising 20 to 300 mg of methylthioninium chloride dihydrate Form B, C or D or methylthioninium chloride monohydrate Form E as described herein, and a pharmaceutically acceptable carrier, diluent; or excipient.

In one embodiment, the dosage unit is a tablet.
In one embodiment, the dosage unit is a capsule.
In one embodiment, the amount is 20 to 200 mg.
In one embodiment, the amount is about 20 mg.
In one embodiment, the amount is about 60 mg.
In one embodiment, the amount is about 100 mg.
In one embodiment, the amount is about 150 mg.
In one embodiment, the amount is about 200 mg.

In one embodiment, the pharmaceutically acceptable carrier, diluent, or excipient is or comprises one or both of a glyceride (e.g., Gelucire 44/14®; lauroyl macrogol-32 glycerides PhEur, USP) and colloidal silicon dioxide (e.g., 2% Aerosil 200®; Colliodal Silicon Dioxide PhEur, USP).

Dosage

It will be appreciated by one of skill in the art that appropriate dosages of methylthioninium chloride dihydrate Form B, C or D or methylthioninium chloride monohydrate Form E, and compositions comprising methylthioninium chloride dihydrate Form B, C or D or methylthioninium chloride monohydrate Form E, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of methylthioninium chloride dihydrate Form B, C or D or methylthioninium chloride monohydrate Form E is in the range of about 100 ng to about 25 mg (more typically about 1 µg to about 10 mg) per kilogram body weight of the subject per day.

In one embodiment, methylthioninium chloride dihydrate Form B, C or D or methylthioninium chloride monohydrate Form E is administered to a human patient according to the following dosage regime: about 100 mg, 3 times daily.

In one embodiment, methylthioninium chloride dihydrate Form B, C or D or methylthioninium chloride monohydrate Form E is administered to a human patient according to the following dosage regime: about 150 mg, 2 times daily.

In one embodiment, methylthioninium chloride dihydrate Form B, C or D or methylthioninium chloride monohydrate Form E is administered to a human patient according to the following dosage regime: about 200 mg, 2 times daily.

The following examples illustrate the present invention without limiting the described scope.

EXPERIMENTAL

Powder X-ray Diffraction (PXRD): PXRD was performed on a Bruker D8 Advance powder X-ray diffractometer using CuKα radiation. D-spacings are calculated from the 2θ values using the wavelength of 1.54180 Å. Generally, 2θ values are within an error of ±0.1-0.2°. The experimental error on the d-spacing values is therefore dependent on the peak location.

Differential Scanning calorimetry (DSC): Perkin Elmer DSC 7, measurements performed in gold sample pan hermetically sealed under ambient conditions. A heating rate of either 20 K/min or 100 K/min was used. All herein given melting points are determined from the peak temperatures of the DSC measurements.

Thermogravimetry (TG): Perkin Elmer TGS 2. Aluminium crucible (open), $N_2$ atmosphere, heating rate 10° C. $min^{-1}$, range 25-350° C.

Thermogravimetric measurements with IR detection (TG-FTIR): Netzsch Thermo-Microbalance TG 209 coupled to a Bruker FTIR Spectrometer Vector 22 (sample pans with pinhole, nitrogen atmosphere, heating rate 10 K/min).

Hydrate Form A

Methylthioninium chloride pentahydrate Form A maybe obtained by re-crystallization of the product prepared according to WO 2006/032879 from 0.1 M hydrochloric acid and drying in vacuum at about 60 mbar and room temperature (see Example 17). As a comparison, d-values (Å) are given in table 1 for form A.

TABLE 1

| d-Spacings for crystal Form A | | |
|---|---|---|
| Angle [° 2θ] | d-spacing [Å] | Intensity (qualitative) |
| 5.7 | 15.5 | vs |
| 9.2 | 9.6 | vs |
| 9.6 | 9.2 | vs |
| 10.8 | 8.2 | s |
| 11.3 | 7.8 | m |
| 18.7 | 4.75 | vs |
| 19.3 | 4.60 | s |
| 20.4 | 4.35 | m |
| 21.7 | 4.10 | m |
| 21.9 | 4.06 | m |
| 24.6 | 3.62 | m |
| 25.6 | 3.48 | vs |

TABLE 1-continued d-Spacings for crystal Form A

| Angle [° 2θ] | d-spacing [Å] | Intensity (qualitative) |
|---|---|---|
| 26.0 | 3.43 | s |
| 26.2 | 3.40 | vs |
| 26.4 | 3.38 | vs |
| 27.3 | 3.27 | s |
| 28.0 | 3.19 | s |
| 28.4 | 3.14 | s |
| 29.2 | 3.06 | m |

The abbreviations in brackets mean: (vs)=very strong intensity; (s)=strong intensity; (m)=medium intensity; and (w)=weak intensity.

Characteristic IR signals of form A in ATR-IR are found at 1491, 1421, 1356, 1225/1215 (double peak), 1177, and 1151 $cm^{-1}$.

A) Preparation of Polymorph Form B

Example A1

Figure 1:
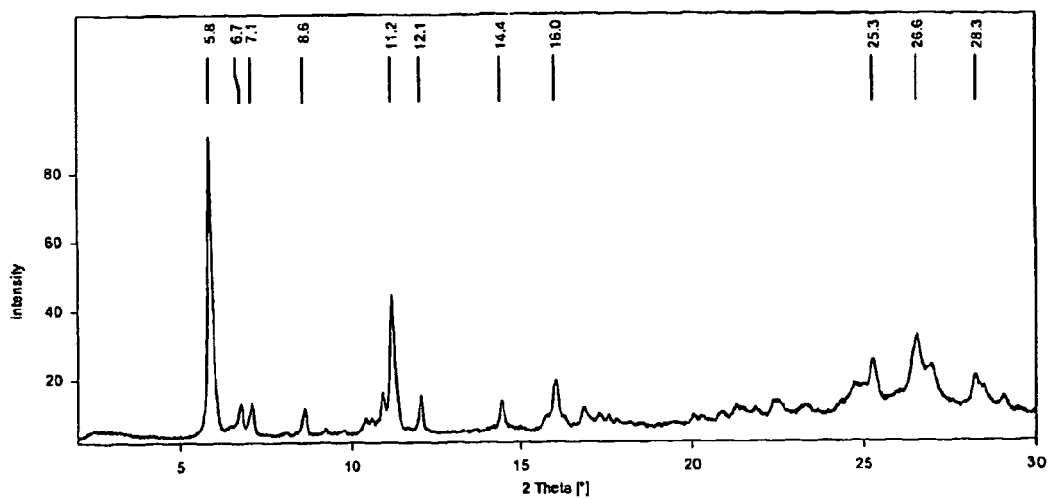
FIG. 1 is a characteristic X-ray powder diffraction pattern of the crystalline water containing Form B of methylthioninium chloride.

150 mg of crystalline methylthioninium chloride pentahydrate are heated to 60° C. for 5 days at 35% r.h. Thermogravimetry on the product shows a weight loss of 10.6% up to a temperature of 150° C., which corresponds to the presence of two equivalents of water. PXRD revealed a crystalline sample. The powder X-ray diffraction pattern is shown in FIG. 1 and the characteristic peaks in N with the corresponding d-spacing values in A are given in table 2. DSC (–50° C. to 210° C., 100° C./min, gold crucible) revealed a melting peak at 186° C. with a shoulder towards lower temperature.

TABLE 2 d-Spacings for hydrate Form B

| Angle [° 2θ] | d-spacing [Å] | Intensity (qualitative) |
|---|---|---|
| 5.8 | 15.2 | S |
| 9.2 | 9.6 | W |
| 11.2 | 7.9 | M |
| 15.6 | 5.68 | W |
| 16.9 | 5.25 | W |
| 20.6 | 4.31 | W |
| 25.3 | 3.52 | M |
| 26.8 | 3.33 | M |
| 28.3 | 3.15 | W |

Example A2

1 g of crystalline methylthioninium chloride pentahydrate Form A powder, contaminated with a small amount of form B, was stored at room temperature for 3 weeks under stirring with a small magnetic stirrer under a flow of humidified nitrogen having approximately 9% relative humidity. Dehydration is complete after 3 weeks and yields quantitatively methylthioninium chloride dihydrate Form B as greenish crystal powder. PXRD corresponds to that of example A1.

Example A3

2 g of crystalline methylthioninium chloride pentahydrate Form A powder, contaminated with a small amount of form B, was stored at room temperature for 4 weeks under stirring with a small magnetic stirrer under a flow of humidified nitrogen having approximately 14% r.h. Dehydration is complete after 3 weeks and yields quantitatively methylthioninium chloride dihydrate Form B as greenish crystal powder. PXRD corresponds to that of example A1.

B) Preparation of Polymorph Form C

Example B1

A mixture of methylthioninium chloride pentahydrate Form A and methylthioninium chloride dihydrate Form B (170 mg) was suspended in 2 ml acetonitrile and stirred at room temperature for 4 days. The solid was filtered off and dried in vacuum at 1 mbar and at room temperature for 15 minutes. 110 mg of methylthioninium chloride dihydrate Form C were obtained as greenish crystal powder.

Figure 2:
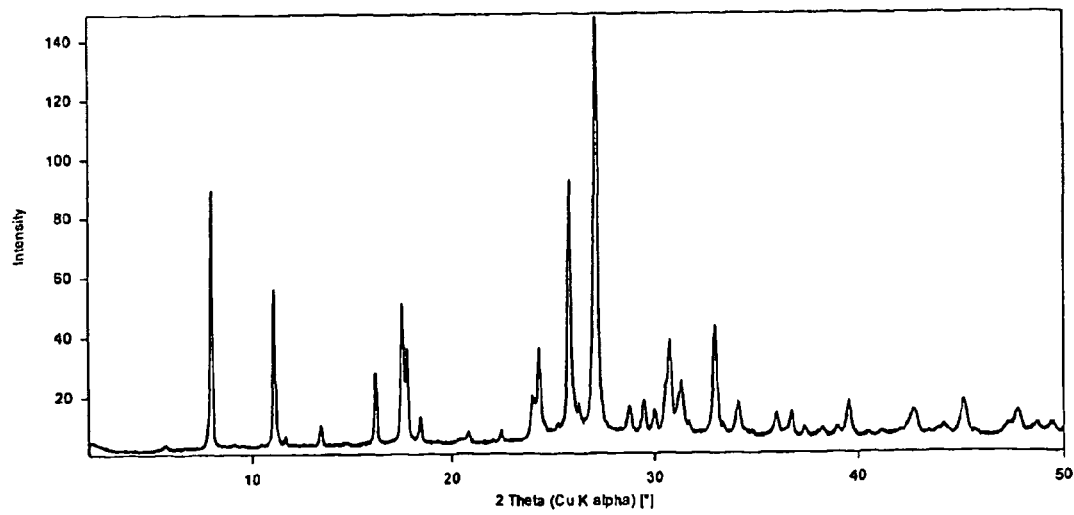
FIG. 2 is a characteristic X-ray powder diffraction pattern of the crystalline dihydrate of methylthioninium chloride Form C.

PXRD revealed a crystalline sample. The powder X-ray diffraction pattern is shown in FIG. 2 and the characteristic peaks in 2θ with the corresponding d-spacing values in A are given in table 3. TG-FTIR revealed a mass kiss of about 11.4% in two steps between room temperature and 150° C., which corresponds to a water content of 2.2 equivalents, which is slightly more than expected for the dihydrate. DSC (–50° C. to 210° C., 100° C./min, gold crucible) revealed two endothermic peaks at 151° C. and 183° C.

TABLE 3 d-Spacings for hydrate Form C

| Angle [° 2θ] | d-spacing [Å] | Intensity (qualitative) |
|---|---|---|
| 8.1 | 10.9 | vs |
| 11.1 | 8.0 | s |
| 13.4 | 6.6 | w |
| 16.2 | 5.47 | m |
| 17.6 | 5.04 | s |
| 17.8 | 4.98 | m |
| 18.4 | 4.82 | w |
| 24.4 | 3.65 | m |
| 25.9 | 3.44 | vs |
| 27.2 | 3.28 | vs |
| 28.7 | 3.11 | w |
| 29.5 | 3.03 | w |
| 30.0 | 2.98 | w |
| 30.8 | 2.90 | m |
| 31.3 | 2.86 | m |
| 33.0 | 2.71 | m |
| 34.1 | 2.63 | w |
| 36.0 | 2.49 | w |
| 36.7 | 2.45 | w |
| 39.5 | 2.28 | w |
| 42.7 | 2.12 | w |
| 45.3 | 2.00 | w |
| 48.0 | 1.90 | w |

Example B2

175 mg of a mixture of methylthioninium chloride pentahydrate Form A and methylthioninium chloride dihydrate Form B was dissolved at about 100° C. in 3 ml dimethylsulfoxide (DMSO). The solution was allowed to cool to room temperature and stored overnight in a refrigerator. The cool solid mixture was allowed to warm to room temperature, whereby DMSO melts. The remaining solid was filtered off and dried in vacuo at 1 mbar and at room temperature. This yields 135 mg greenish methylthioninium chloride dihydrate Form C. The PXRD corresponds to that of example B1.

Example B3

2 g of methylthioninium chloride pentahydrate Form A was suspended in 10 ml acetonitrile and stirred at room temperature for 6 days. The solid was filtered off and dried in vacuo at 1 mbar and at room temperature for 15 minutes. This procedure was repeated two times. Pure methylthioninium chloride dihydrate Form C was obtained as greenish crystal powder. The PXRD corresponds to that of example B1. Thermogravimetry revealed a mass loss of 9.8% in two steps between room temperature and 150° C. The total mass loss corresponds almost exactly to a water content of 2 equivalents.

Example B4

100 mg of a mixture comprising methylthioninium chloride pentahydrate Form A, methylthioninium chloride dihydrate Form B, methylthioninium chloride dihydrate Form C and methylthioninium chloride dihydrate Form p were suspended in 2 ml isopropanol containing 20 μl water (corresponding to about 12% relative humidity). The suspension was stirred at room temperature for 6 days. The solid is filtered off and dried in vacuum at 1 mbar and at room temperature for 5 minutes. This yielded pure methylthioninium chloride dihydrate form C as greenish crystal powder. The PXRD corresponds to that of example B1.

Example B5

100 mg of a mixture comprising methylthioninium chloride pentahydrate Form A, methylthioninium chloride dihydrate Form B, methylthioninium chloride dihydrate Form C and methylthioninium chloride dihydrate Form D were suspended in 2 ml isopropanol containing 50 μl water (about 28% r.h.). The suspension was stirred at room temperature for 6 days. The solid was filtered off and dried under vacuum at 1 mbar and at room temperature for 5 minutes. This yielded pure methylthioninium chloride dihydrate form C as greenish crystal powder. The PXRD corresponds to that of example B1.

100 mg of the powdery product was pressed to a tablet at a pressure of 1 to/0.5 cm². Form C was retained in the tablet. The PXRD corresponds to that of example B1.

Example B6

500 mg of methylthioninium chloride pentahydrate Form A was suspended in 10 ml isopropanol and stirred for 2 weeks. The solid was filtered off and dried under vacuum at 1 mbar and at room temperature for 5 minutes. This yielded methylthioninium chloride dihydrate form C as greenish crystal powder. The PXRD corresponds to that of example B1.

C) Preparation of Hydrate Form D

Example C1

100 mg of methylthioninium chloride dihydrate Form B were dissolved in 2 ml pure acetic acid. The solution was filtered through a 0.2 μm syringe filter and added to 10 ml toluene. A sticky precipitate forms within a short time. The solid was filtered off about 3 minutes after precipitation, washed with toluene and dried under vacuum at 1 mbar and at room temperature for 15 minutes. This yields 70 mg of methylthioninium chloride dihydrate form D as grey to violet crystal powder.

Figure 3:
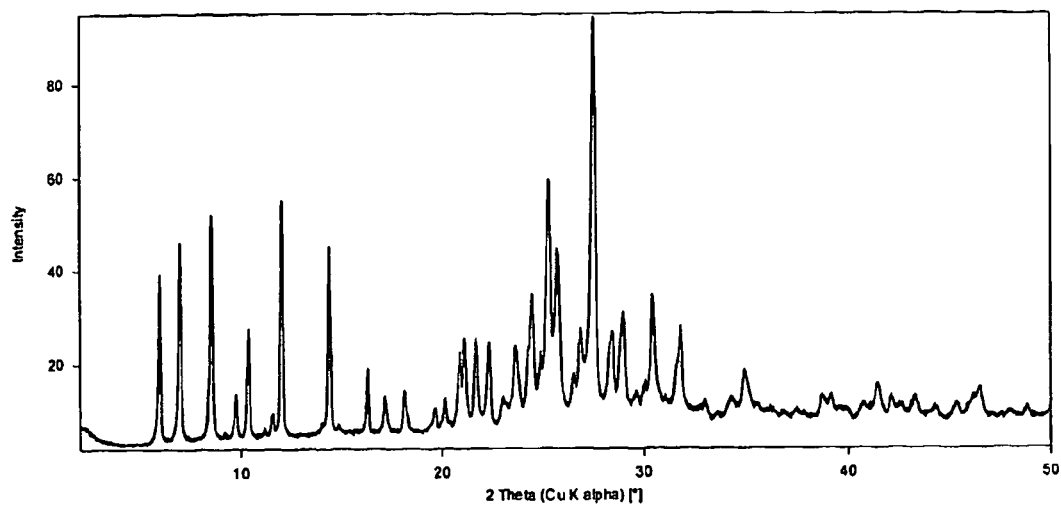
FIG. 3 is a characteristic X-ray powder diffraction pattern of the crystalline dihydrate of methylthioninium chloride Form D.

PXRD revealed a crystalline sample. The powder X-ray diffraction pattern is shown in FIG. 3 and the characteristic peaks in 2θ with the corresponding d-spacing values in Å are given in table 4. TG revealed a mass loss of about 9.3% and TG-FTIR revealed a mass loss of about 11.0% between room temperature and 150° C., which corresponds to a water content of 2.2 equivalents, which is slightly more than expected for the dihydrate. DSC (−50° C. to 210° C., 100° C./min, gold crucible) revealed two endothermic peaks at 164° C. and 185° C.

TABLE 3 d-Spacings for polymorph Form D

| Angle [° 2θ] | d-spacing [Å] | Intensity (qualitative) |
|---|---|---|
| 6.0 | 14.7 | m |
| 7.0 | 12.6 | s |
| 8.5 | 10.4 | s |
| 9.8 | 9.0 | w |
| 10.4 | 8.5 | m |
| 12.0 | 7.4 | s |
| 14.4 | 6.2 | s |
| 16.3 | 5.44 | w |
| 17.1 | 5.19 | w |
| 18.1 | 4.90 | w |
| 20.9 | 4.25 | m |
| 21.1 | 4.21 | m |
| 21.7 | 4.10 | m |
| 22.3 | 3.99 | m |
| 23.7 | 3.75 | m |
| 24.5 | 3.63 | m |
| 25.3 | 3.52 | s |
| 25.7 | 3.47 | s |
| 26.9 | 3.31 | m |
| 27.5 | 3.24 | vs |
| 28.5 | 3.13 | m |
| 29.0 | 3.08 | m |
| 30.4 | 2.94 | m |
| 31.8 | 2.81 | m |
| 34.9 | 2.57 | w |
| 41.5 | 2.18 | w |
| 46.5 | 1.95 | w |

Example C2

118 mg of methyithioninium chloride pentahydrate Form A were dissolved in 2 ml pure acetic acid. The solution was filtered through a 0.2 μm syringe filter and added to 10 ml toluene. A sticky precipitate forms within a short time. The solid was filtered off about 3 minutes after precipitation, washed with toluene and dried at room temperature for 60 minutes. This yielded methyithioninium chloride dihydrate form D as a grey to violet crystal powder. The PXRD corresponds to that of example C1.

Example C3

1 g of methyithioninium chloride pentahydrate Form A were dissolved in 10 ml methanol. The solution is filtered through a 0.2 μm syringe filter and added without stirring to 100 ml t-butyl-methyl ether (tBME). A precipitate forms within short time. The solid was filtered off about 3 minutes after precipitation, washed with tBME and dried in a flow of nitrogen for 1 hour. This yields 850 mg of methylthioninium chloride dihydrate form D as grey-violet crystal powder. The PXRD corresponds to that of example C1.

D) Preparation of Hydrate Form E

Example D1

80 mg of a mixture comprising methylthioninium chloride pentahydrate Form A, methylthioninium chloride dihydrate Form B, methylthioninium chloride dihydrate Form C and methylthioninium chloride dihydrate Form D were suspended in 2 ml dry isopropanol containing less than 0.1% by weight of water. The suspension was stirred under temperature cycling between 25° C. and 35° C. for 1 week. The solid was filtered and dried under vacuum at 1 mbar and at room temperature for 5 minutes. This yielded methylthioninium chloride monohydrate form E as ocher crystal powder.

Figure 4:
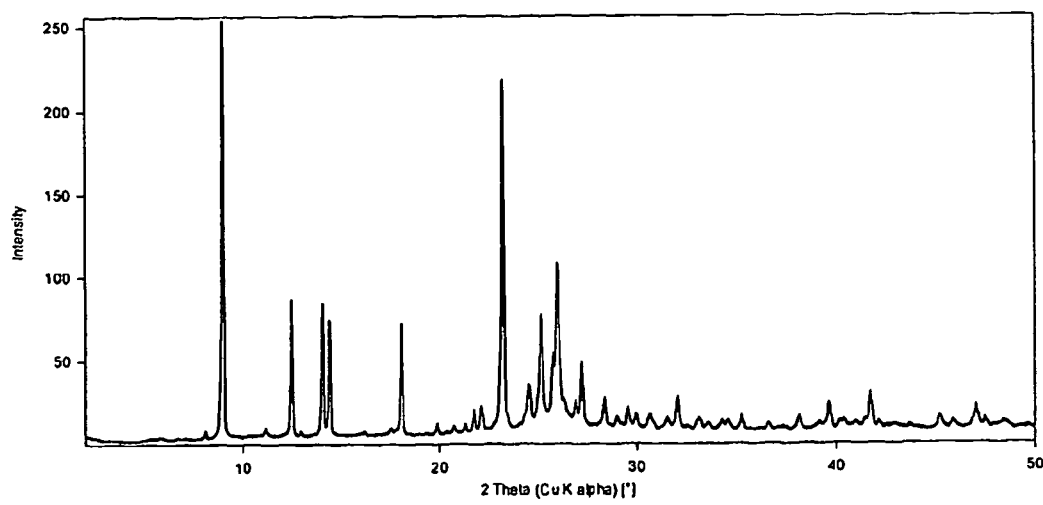
FIG. 4 is a characteristic X-ray powder diffraction pattern of the crystalline monohydrate of methylthioninium chloride Form E.

PXRD revealed a crystalline sample. The powder X-ray diffraction pattern is shown in FIG. 4 and the characteristic peaks in 2θ with the corresponding d-spacing values in Å are given in table 5. TG revealed a mass loss of about 5.1% between room temperature and 125° C., which corresponds to a water content of 1 equivalent. DSC (−50° C. to 210° C., 100° C./min, gold crucible) revealed no thermal events up to the decomposition temperature of about 200° C.

TABLE 3 d-Spacings for polymorph Form E

| Angle [° 2θ] | d-spacing [Å] | Intensity (qualitative) |
| --- | --- | --- |
| 9.0 | 9.8 | vs |
| 12.5 | 7.1 | s |
| 14.1 | 6.3 | s |
| 14.4 | 6.2 | s |
| 18.1 | 4.90 | s |
| 21.8 | 4.08 | w |
| 22.1 | 4.02 | w |
| 23.2 | 3.83 | vs |
| 24.5 | 3.63 | m |
| 25.1 | 3.55 | s |
| 26.0 | 3.43 | vs |
| 27.2 | 3.28 | m |
| 28.4 | 3.14 | w |
| 29.6 | 3.02 | w |
| 32.0 | 2.80 | w |
| 39.6 | 2.28 | w |
| 41.7 | 2.17 | w |
| 47.1 | 1.93 | w |

Example D2

1 g of methylthioninium chloride pentahydrate Form A was suspended in 20 ml dry isopropanol and stirred at room temperature for 3 days. The solid was filtered off, re-suspended in 10 ml dry isopropanol and stirred for another 9 days. The solid was filtered off again. When becoming solvent-free, the filter cake turns to ocher color. Residual isopropanol is removed under a dry nitrogen flow for 2 hours. This yields 700 mg of methylthioninium chloride monohydrate form E as an ocher crystalline powder. The PXRD corresponds to that of example D1.

Example D3

1 g of methylthioninium chloride pentahydrate Form A was suspended in 10 ml dry isopropanol and stirred at room temperature for 1 day. The solid was filtered off, again suspended in 10 ml dry isopropanol and stirred for 3 days. Filtration, re-suspension and stirring was repeated once again. The solid turns to ocher color. Finally, the ocher solid was filtered off and residual isopropanol is removed under a dry nitrogen flow for 2 hours. This yields 650 mg of methylthioninium chloride monohydrate form E as an ochre crystalline powder. The PXRD corresponds to that of example D1.

The invention claimed is:

1. Crystalline methylthioninium chloride dihydrate as Form C, having the following characteristic peaks in a powder X-ray diffraction pattern:

| Peak | 2θ values (±0.1°) |
| --- | --- |
| 1 | 8.1 |
| 2 | 11.1 |
| 3 | 17.6 |
| 4 | 25.9 |
| 5 | 27.2. |

2. The compound of claim 1 having the following additional characteristic peaks in a powder X-ray diffraction pattern:

| Peak | 2θ values (±0.1°) |
| --- | --- |
| 6 | 16.2 |
| 7 | 17.8 |
| 8 | 24.4 |
| 9 | 30.8 |
| 10 | 31.3 |
| 11 | 33.0. |

3. The compound of claim 1, which has two endothermic maxima at 151° C. and 183° C. when heated at a rate of 100° C. per minute in Differential Scanning calorimetry.

4. A process for the preparation of methylthioninium chloride dihydrate substantially in form C according to claim 1, wherein a water-containing methylthioninium chloride or a mixture of various hydrates or a specific hydrate thereof is suspended and stirred at ambient temperature in a solvent selected from the group comprising isopropanol, 1-propanol, 1-butanol, 2-butanol, tert.-butanol, tetrahydrofurane, dioxane, acetone, 2-butanone, and acetonitrile containing a small amount of water, for a time sufficient to generate form C; the solid is then isolated; and the solvent is removed from the solid.

5. Crystalline methylthioninium chloride dihydrate as Form D, having the following characteristic peaks in a powder X-ray diffraction pattern:

| Peak | 2θ values (±0.1°) |
| --- | --- |
| 1 | 7.0 |
| 2 | 8.5 |
| 3 | 12.0 |
| 4 | 14.4 |
| 5 | 25.3 |
| 6 | 25.7 |
| 7 | 27.5. |

6. The compound of claim 5 having the following additional characteristic peaks in a powder X-ray diffraction pattern:

| Peak | 2θ values (±0.1°) |
| --- | --- |
| 8 | 6.0 |
| 9 | 10.4 |
| 10 | 20.9 |
| 11 | 21.1 |
| 12 | 21.7 |
| 13 | 22.3 |
| 14 | 23.7 |
| 15 | 24.5 |
| 16 | 26.9 |
| 17 | 28.5 |
| 18 | 29.0 |
| 19 | 30.4 |
| 20 | 31.8. |

7. The compound of claim 5, which has two endothermic peak maxima at 164° C. and 185° C. and a step in the baseline near 63° C. when heated at a rate of 100° C. per minute in Differential Scanning calorimetry.

8. A process for the preparation of methylthioninium chloride dihydrate substantially in form D according to claim 5, comprising: dissolving methylthioninium chloride pentahydrate in acetic acid and combining the solution with toluene, either by adding toluene to the acetic acid solution or by adding the acetic acid solution to toluene; isolating the solid by filtration shortly after precipitation; and removing the solvent by vacuum drying or in an inert gas flow, whereby the relative air humidity in all process steps is less than 50%.

9. Crystalline methylthioninium chloride dihydrate substantially as Form B, having the following characteristic peaks in a powder X-ray diffraction pattern:

| Peak | 2θ values (±0.1°) |
|---|---|
| 1 | 5.8 |
| 2 | 11.2 |
| 3 | 25.3 |
| 4 | 26.8. |

10. The compound of claim 9 having the following additional characteristic peaks in a powder X-ray diffraction pattern:

| Peak | 2θ values (±0.1°) |
|---|---|
| 5 | 15.6 |
| 6 | 16.9 |
| 7 | 20.3 |
| 8 | 28.3. |

11. The compound of claim 9, which has a melting peak at 186° C. with a shoulder towards lower temperature when heated at a rate of 100° C. per minute in Differential Scanning calorimetry.

12. A process for the preparation of methylthioninium chloride dihydrate substantially in form B of claim 9, which comprises exposing solid methylthioninium chloride pentahydrate at about room temperature to an inert gas flow having a relative humidity from 8 to 15% for a time sufficient to generate essentially pure form B.

13. A pharmaceutical composition comprising methylthioninium chloride dihydrate form B, C or D and optionally a pharmaceutically acceptable carrier, excipient or diluent; wherein Form B has the following characteristic peaks in a powder X-ray diffraction pattern:

| Peak | 2θ values (±0.1°) |
|---|---|
| 1 | 5.8 |
| 2 | 11.2 |
| 3 | 25.3 |
| 4 | 26.8; |

Form C has the following characteristic peaks in a powder X-ray diffraction pattern:

| Peak | 2θ values (±0.1°) |
|---|---|
| 1 | 8.1 |
| 2 | 11.1 |
| 3 | 17.6 |
| 4 | 25.9 |
| 5 | 27.2 | and;

Form D has the following characteristic peaks in a powder X-ray diffraction pattern:

| Peak | 2θ values (±0.1°) |
|---|---|
| 1 | 7.0 |
| 2 | 8.5 |
| 3 | 12.0 |
| 4 | 14.4 |
| 5 | 25.3 |
| 6 | 25.7 |
| 7 | 27.5. |

14. A method of treatment of a tauopathy, Alzheimer's disease (AD), skin cancer, melanoma, Hepatitis C, HIV or West Nile virus in a patient, comprising administering to said patient a therapeutically-effective amount of methylthioninium chloride dihydrate form B, C or D; wherein Form B has the following characteristic peaks in a powder X-ray diffraction pattern:

| Peak | 2θ values (±0.1°) |
|---|---|
| 1 | 5.8 |
| 2 | 11.2 |
| 3 | 25.3 |
| 4 | 26.8; |

Form C has the following characteristic peaks in a powder X-ray diffraction pattern:

| Peak | 2θ values (±0.1°) |
|---|---|
| 1 | 8.1 |
| 2 | 11.1 |
| 3 | 17.6 |
| 4 | 25.9 |
| 5 | 27.2 | and;

Form D has the following characteristic peaks in a powder X-ray diffraction pattern:

| Peak | 2θ values (±0.1°) |
|---|---|
| 1 | 7.0 |
| 2 | 8.5 |
| 3 | 12.0 |
| 4 | 14.4 |
| 5 | 25.3 |
| 6 | 25.7 |
| 7 | 27.5. |

* * * * *